United States Patent
Mountney et al.

(10) Patent No.: US 9,687,204 B2
(45) Date of Patent: Jun. 27, 2017

(54) METHOD AND SYSTEM FOR REGISTRATION OF ULTRASOUND AND PHYSIOLOGICAL MODELS TO X-RAY FLUOROSCOPIC IMAGES

(75) Inventors: Peter Mountney, Plainsboro, NJ (US); Markus Kaiser, Forchheim (DE); Ingmar Voigt, Erlangen (DE); Matthias John, Nürnberg (DE); Razvan Ioan Ionasec, Lawrenceville, NJ (US); Jan Boese, Eckental (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 471 days.

(21) Appl. No.: 13/475,048

(22) Filed: May 18, 2012

(65) Prior Publication Data
US 2012/0296202 A1    Nov. 22, 2012

Related U.S. Application Data

(60) Provisional application No. 61/488,241, filed on May 20, 2011.

(51) Int. Cl.
*A61B 6/12* (2006.01)
*A61B 6/00* (2006.01)
(Continued)

(52) U.S. Cl.
CPC .............. *A61B 6/12* (2013.01); *A61B 6/4417* (2013.01); *A61B 6/487* (2013.01); *A61B 6/5247* (2013.01);
(Continued)

(58) Field of Classification Search
CPC ... A61B 8/5261; G06T 7/0024; G06T 7/0032; G06T 7/004; G06T 7/0046
(Continued)

(56) References Cited

U.S. PATENT DOCUMENTS 7,517,318 B2 *   4/2009   Altmann et al. .............. 600/459

OTHER PUBLICATIONS

Rapid Image Registration of Three-Dimensional Transesophageal Echocardiography and X-ray Fluoroscopy for the Guidance of Cardiac Interventions by G. Gao et al. Lecture Notes in Computer Science. vol. 6135. pp. 124-134. 2010.*
(Continued)

*Primary Examiner* — Tse Chen
*Assistant Examiner* — Jason Ip

(57) ABSTRACT

A method and system for registering ultrasound images and physiological models to x-ray fluoroscopy images is disclosed. A fluoroscopic image and an ultrasound image, such as a Transesophageal Echocardiography (TEE) image, are received. A 2D location of an ultrasound probe is detected in the fluoroscopic image. A 3D pose of the ultrasound probe is estimated based on the detected 2D location of the ultrasound probe in the fluoroscopic image. The ultrasound image is mapped to a 3D coordinate system of a fluoroscopic image acquisition device used to acquire the fluoroscopic image based on the estimated 3D pose of the ultrasound probe. The ultrasound image can then be projected into the fluoroscopic image using a projection matrix associated with the fluoroscopic image. A patient specific physiological model can be detected in the ultrasound image and projected into the fluoroscopic image.

20 Claims, 6 Drawing Sheets

(51) Int. Cl.
   *A61B 8/08*  (2006.01)
   *A61B 8/00*  (2006.01)
   *A61B 8/12*  (2006.01)

(52) U.S. Cl.
   CPC .............. *A61B 8/0841* (2013.01); *A61B 8/12* (2013.01); *A61B 8/4245* (2013.01); *A61B 8/4416* (2013.01); *A61B 8/5261* (2013.01); *A61B 6/4441* (2013.01); *A61B 6/503* (2013.01); *A61B 8/0883* (2013.01)

(58) Field of Classification Search
   USPC ....... 600/407, 424, 425, 427, 431, 437, 443, 600/444, 445, 446, 447, 462, 463; 128/920, 922; 382/100, 128, 132, 155, 382/159, 276, 285, 293, 294
   See application file for complete search history.

(56) References Cited

OTHER PUBLICATIONS

Robust Guidewire Tracking in Fluoroscopy by P. Wang et al. IEEE. 9. pp. 691-698. 2009.*
"Hierarchical Learning of Curves, Application to Guidewire Localization in Fluoroscopy" by A. Barbu et al. IEEE Conference on Computer Vision and Pattern Recognition. pp. 1-8. (2007).*

\* cited by examiner

1000

METHOD AND SYSTEM FOR REGISTRATION OF ULTRASOUND AND PHYSIOLOGICAL MODELS TO X-RAY FLUOROSCOPIC IMAGES

This application claims the benefit of U.S. Provisional Application No. 61/488,241, filed May 20, 2011, the disclosure of which is herein incorporated by reference.

BACKGROUND OF THE INVENTION

The present invention relates to registration of multimodal medical images, and more particularly, to registration of ultrasound images and physiological models to x-ray fluoroscopic images.

In recent years, there has been a major trend in cardiac therapy towards minimally invasive transcatheter procedures to reduce the risks involved with classical surgical techniques. For example, such minimally invasive surgical techniques can be used in procedures such as aortic valve replacement. In such minimally invasive cardiac surgeries, devices such as implants are delivered into the patient through vessels via a catheter. Navigating the catheter inside the vessels of a patient is challenging. X-ray fluoroscopy is typically used to visualize the catheter; however, this imaging modality does not capture soft tissue structure of the patient. In order to visualize soft tissue, a second imaging modality, such as Transesophageal Echocardiography (TEE), is required.

Visualization of the catheter and the surrounding soft tissue typically requires two displays, one for each imaging modality. The surgeon must interpret the two separately displayed imaging modalities, extract relevant information, and spatially transform the information between the two coordinate systems and ultimately into the patient. The fusion of fluoroscopy and ultrasound images into a single visualization is desirable and to simply navigation in transcatheter procedures.

BRIEF SUMMARY OF THE INVENTION

The present invention provides a method and system for registration or fusion of ultrasound and x-ray fluoroscopic images. The present invention also provides a method and system for registering patient-specific physiological models to x-ray fluoroscopic images. Embodiments of the present invention estimate a 3D six degree of freedom (DOF) transformation between an ultrasound image and a fluoroscopic image. This transformation in conjunction with device calibration parameters is used to fuse the imaging modalities.

In one embodiment of the present invention, a 2D location of an ultrasound probe is detected in a fluoroscopic image acquired using a fluoroscopic image acquisition device. A 3D pose of the ultrasound probe is estimated based on the detected 2D location of the ultrasound probe in the fluoroscopic image. An ultrasound image is mapped to a 3D coordinate system of the fluoroscopic image acquisition device based on the estimated 3D pose of the ultrasound probe. The ultrasound image can then be projected into the fluoroscopic image using a projection matrix associated with the fluoroscopic image. A patient specific physiological model can also be detected in the ultrasound image and projected into the fluoroscopic image.

These and other advantages of the invention will be apparent to those of ordinary skill in the art by reference to the following detailed description and the accompanying drawings.

DETAILED DESCRIPTION

Figure 1:
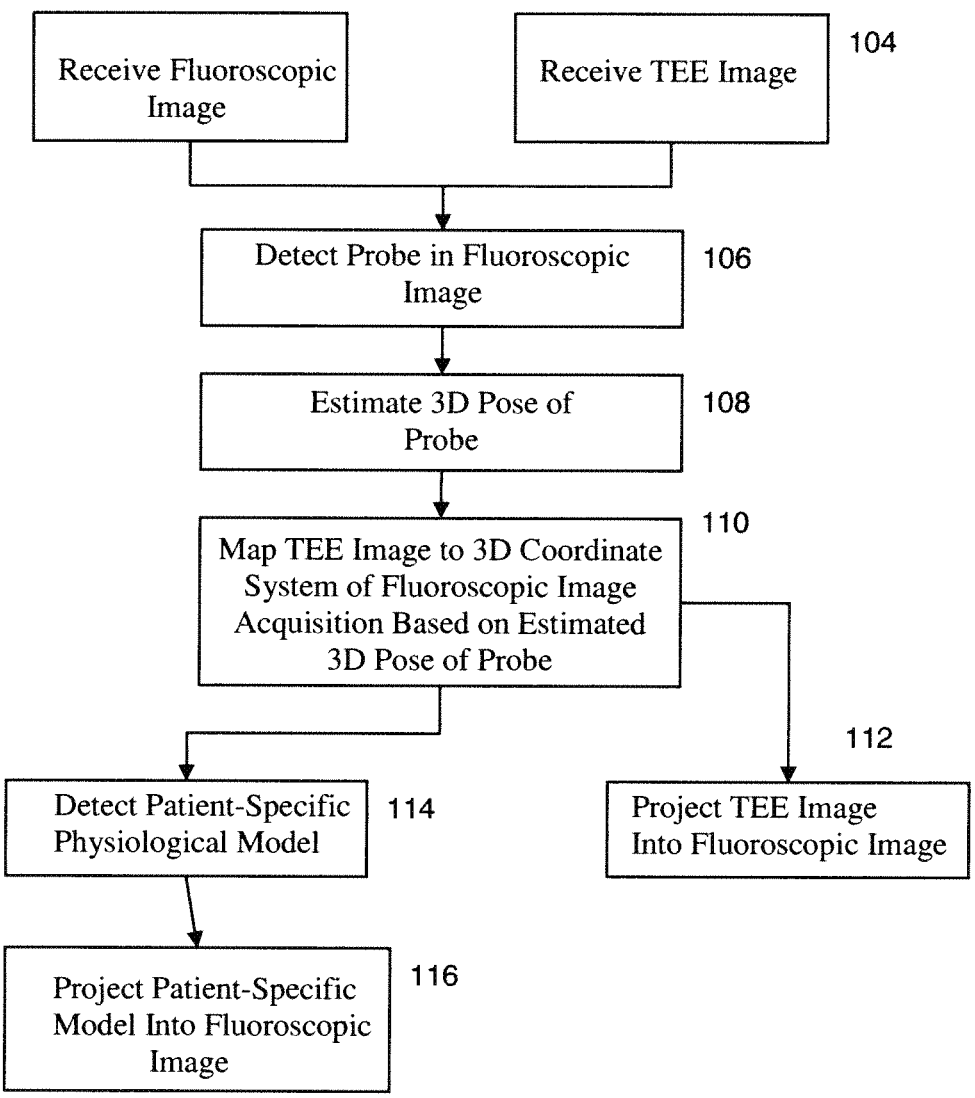
FIG. 1 illustrates a method for registering ultrasound and x-ray fluoroscopy images according to an embodiment of the present invention.

The present invention relates to registration of ultrasound and physiological models to x-ray fluoroscopic images. Embodiments of the present invention are described herein to give a visual understanding of the model-based image fusion method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Methods that attempt fusion of ultrasound and x-ray fluoroscopy can be broadly categorized as either hardware based or image based. Hardware based approaches typically attach additional devices to an ultrasound probe (used to acquire Transesophageal Echocardiography (TEE) images) such as electromagnetic trackers or mechanical/robotic devices. These devices track the position and orientation of the probe in a coordinate system defined by the tracking device. Through a calibration process, the transformation between the ultrasound image and the tracked point on the probe is estimated. This transformation is rigid and does not change during a procedure. A second calibration procedure estimates the transformation between the tracking device coordinate system and the x-ray fluoroscopy device. Concatenating these transformations registers the ultrasound image to the x-ray fluoroscopy image. It is typically assumed in such cases that the ultrasound image is not rotated or zoomed.

The introduction of additional hardware into the already crowded operating theatre, as required by hardware based approaches, is not desirable and can require time consuming configuration and be disruptive to the workflow involved in transcatheter procedures. Additionally, electromagnetic trackers can suffer from noise and interference, leading to inaccuracies, and mechanical/robotic devices that have been proposed are not suitable for invasive procedures and must be located outside the patient.

Image based registration techniques use information extracted from the images to fuse ultrasound and x-ray fluoroscopy images. An image based method is described in Gao et al., "Rapid Image Registration of Three-Dimensional Transesophageal Echocardiography and X-ray Fluoroscopy for the Guidance of Cardiac Interventions", In *Proceedings of the First International Conference on Information Processing in Computer-Assisted Interventions,* 2010, pages 124-134 and Gao et al., "Registration of 3D Trans-esophageal Echocardiography to X-ray Fluoroscopy Using Image-Based Probe Tracking," *Medical Image Analysis,* 2011, the disclosures of which are incorporated herein by reference. The method iteratively generates Digitally Reconstructed Radiograph (DRR) images and registers them to fluoroscopic images. A gradient difference similarity measure is used in conjunction with a Powell optimizer. Image based fusion is advantageous as it does not require addition equipment to be integrated into the operating theatre. However, the proposed approach requires manual initialization and cannot cope with large inter frame motion or registration failure. The approach requires two x-ray fluoroscopy images for accurate estimation of the probes position inn the axis of the x-ray imaging device and is computationally expensive (e.g., 9.5 seconds per frame), which may be prohibitive for use in real-time during cardiac procedures.

Embodiments of the present invention provide a method of registering ultrasound (e.g., TEE) and x-ray fluoroscopy images. In various embodiments of the present invention, ultrasound probe detection enables robust probe estimation even with large inter frame motion. Various embodiments use learning based methods, which are robust to noise and large variations in appearance. Using such learning based methods, the type and/or make of the probe can be detected as well as the pose of the probe. Various embodiments of the present invention allow a surgeon to visualize an ultrasound image and/or patient specific physiological models in a fluoroscopic workspace. Embodiments of the present invention provide a registration method that can be performed in real time during a cardiac procedure.

Figure 2:
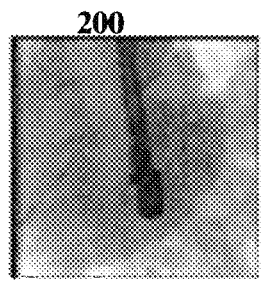
FIG. 2 illustrates an exemplary fluoroscopic image.

FIG. 1 illustrates a method for registering ultrasound and x-ray fluoroscopy images according to an embodiment of the present invention. At step 102, a fluoroscopic image is received. The fluoroscopic image is a 2D x-ray image and can be received directly from an image acquisition device, such as a C-arm image acquisition device. It is to be understood that the fluoroscopic image may be one of a sequence of fluoroscopic images and may be received in real-time during a cardiac intervention procedure. FIG. 2 illustrates an exemplary fluoroscopic image 200.

Returning to FIG. 1, at step 104, a TEE image is received. The TEE image is an ultrasound image that is acquired using a probe with an ultrasound transducer at the tip that is passed into a patient's esophagus. The TEE image may be received directly from the probe in real-time during the cardiac intervention procedure. In an advantageous implementation, the TEE image may be acquired at the same time as the fluoroscopic image received in step 102.

At step 106, the probe is detected in the fluoroscopic image. The probe detection identifies the location of the probe head used in the fluoroscopic image. The probe head is rigid and can move in 3D space with six degrees of freedom (DOF). The probe's location in the fluoroscopic image is defined by two parameters, i.e., the x and y position in the image space. The probe has the potential to move in six DOF and therefore the detection should be robust to changes in scale, translation, and rotation. In clinical practice, the probe's movement is restricted by anatomy and operating room configuration. This prior knowledge can be used to improve detection of the probe's location in the fluoroscopic image.

According to an advantageous implementation, a learning based method can be used for probe detection. Learning based methods are robust to noise and capable of handling large variations in appearance. Unlike matching or similarity measures, learning based methods are trained on a set of manually annotated or synthetically generated training data. In particular, a probe detector is trained using a learning based method offline prior to receiving the fluoroscopic image, and the trained probe detector is used to detect an image patch in the fluoroscopic image that contains the ultrasound probe head. In order to train a probe detector, synthetic data can be generated by using a computed tomography (CT) volume of an ultrasound probe. DRR images are generated from the CT volume of the probe in a variety of known poses. Manually annotated training data is also chosen to contain a wide variety of pose orientations and locations in various fluoroscopic images. Additionally, the training data set can include images without a probe to enable to trained probe detector to correctly classify non-object regions. The training method is generic and independent of the probe type. The training data is probe specific and is performed offline prior to online detection.

In a possible implementation, a probabilistic boosting tree (PBT) can be used to train the probe detector from the training data. The PBT can be trained using Haar features extracted image patches in the training data annotated as positive (belonging to the probe) or negative (belonging to tissue other than the probe). At runtime, in order to detect the probe in the received fluoroscopic image, Haar features are extracted from image patches in the fluoroscopic image and the trained PBT classifier determines a probability score for each image patch. The image patch having the highest probability score is determined to be the position of the probe in the fluoroscopic image.

Figure 3:
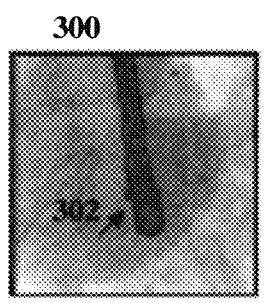
FIG. 3 illustrates probe detection in a fluoroscopic image.

Once the probe is detected in the first frame, a filter, such as an extended Kalman filter or a particle filter, may be used to predict a position of the probe in the next frame. This predicted position can be used to generate a reduced search space. Accordingly, if the fluoroscopic image received at step 102 is a subsequent frame in a sequence of fluoroscopic images, a reduced search space can be determined in the fluoroscopic image based on the probe detection results in the previous frame. In this case, the trained probe detector evaluates only image patches in the reduce search space to detect the probe location. The detected probe location is then used to update the filter state to account for noise in the measurement. FIG. 3 illustrates probe detection in a fluoroscopic image. As shown in FIG. 3, an ultrasound probe 302 is detected in a fluoroscopic image 300 using a trained probe detector.

Returning to FIG. 1, at step 108, a pose of the probe in 3D is estimated. In particular, the pose of the probe relative to the fluoroscopic image is defined by defining the probe's position in 3D (X, Y, Z) and its orientation (roll, pitch, yaw) in the coordinate system of the x-ray fluoroscopic image (i.e., the coordinate system of the C-arm image acquisition device). The detected position of the probe in the 2D fluoroscopic image can be used as a starting point for probe pose estimation using a marginal space learning (MSL) framework.

Figure 4:
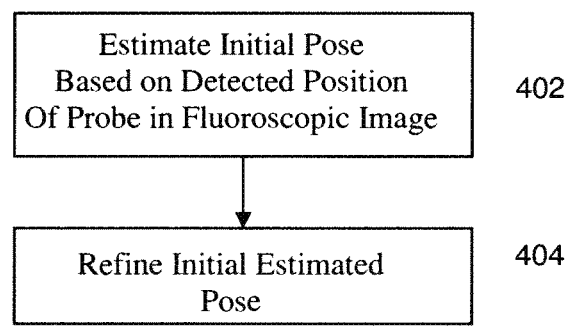
FIG. 4 illustrates a method for estimating the pose according to an embodiment of the present invention.

FIG. 4 illustrates a method for estimating the pose according to an embodiment of the present invention. The method of FIG. 4 can be used to implement step 108 of FIG. 1. As illustrated in FIG. 4, at step 402, an initial pose of the probe is estimated based on the detected position of the probe in the fluoroscopic image. In order to estimate the initial pose of the probe, a marginal space learning approach can be used such that the pose is not estimated directly in the full similarity transformation space, but incrementally on projected sample distributions. This enables fast and directed computation. The 2D position of the probe from the probe detection step is used to initialize pose estimation by estimating the X and Y coordinates of the probe. In order to estimate the pose of the probe in 3D (X, Y, Z) is estimated in a first detection stage, followed by estimation of the position and orientation in a second detection stage.

Learning based techniques are used for each detection stage. This approach treats pose estimation as a classification problem. A training dataset of the probe in different poses is generated offline. The training set can include manually annotated and synthetically generated training data. In a possible implementation, separate PBT classifiers are trained for each detection stage (i.e., position and position-orientation) of the pose estimation. At run time, features (e.g., Haar features) are extracted from the fluoroscopic image and used by the sequence of trained classifiers to estimate the pose of the probe. This approach is fast and provides an initial estimate of the probe's position and orientation.

Similar to as described above in the probe detection step, a filter, such as an extended Kalman filter or a particle filter, can be used to exploit temporal information between the frames. This reduces the search space, enabling the pose of the probe to be predicted in subsequent frames of a fluoroscopic image sequence.

Figure 5:
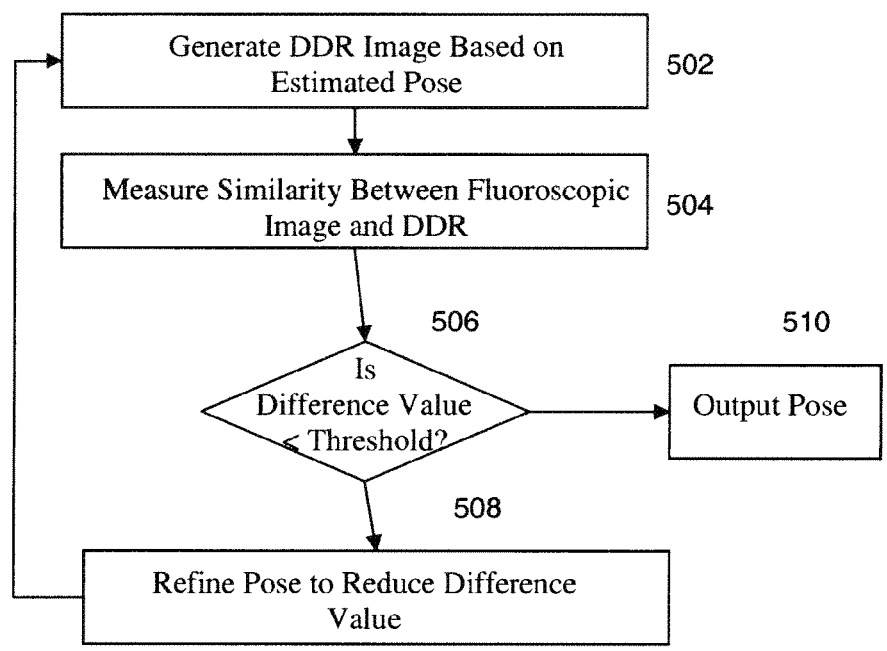
FIG. 5 illustrates a method of refining an estimated pose of an ultrasound probe according to an embodiment of the present invention.

At step 404, the estimated initial pose of the probe is refined. In particular, 2D/3D registration can be used to iteratively refine the pose estimation. FIG. 5 illustrates a method of refining an estimated pose of an ultrasound probe according to an embodiment of the present invention. The method of FIG. 5 can be used to implement step 404 of FIG. 4.

Figure 6:
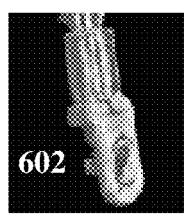
FIG. 6 illustrates a probe in 3D.

At step 502, a DRR image is generated based on the estimated pose of the probe. A 3D model of the probe is generated offline using DynaCT/CT. This model is aligned to the initialized position of the probe in 3D and used to generate a DRR. The DRR produces a representation of the probe which is visually similar to the image captured by the fluoroscopic. This enables a comparison between the two the DRR and the fluoroscopic image. At step 504, similarity between the fluoroscopic image and DRR is measured. The similarity may be measured using a difference value that represents an amount of difference between the fluoroscopic image and the DRR. That is, a small difference value indicates that the fluoroscopic image and the DRR are similar. At step 506, it is determined if the difference value between the fluoroscopic image and the DRR is below of given threshold. If the difference value is not below the threshold at step 506, the method proceeds to step 508. At step 508, the pose is refined based on the measured similarity. The pose can be refined by using a local search to determine a new pose that reduces the difference value measured between the fluoroscopic image and the DRR. After the pose is refined, the method returns to step 502 and a new DRR is generated based on the refined pose. The similarity is then measured between the new DRR and the fluoroscopic image at step 504 and the above described steps are repeated until the difference value is below the threshold. If the difference value is below the threshold at step 506, the method proceeds to step 510. At step 510, the pose of the probe is output and the method ends. FIG. 6 illustrates a probe 602 in 3D. The pose of the probe 602 was determined based on the probe detection results in the fluoroscopic image shown in FIG. 3.

Figure 7:
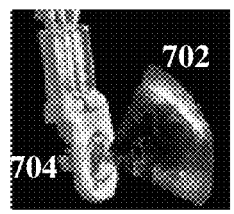
FIG. 7 illustrates a TEE image mapped to a 3D local coordinate system of a fluoroscopic image acquisition device.

Returning to FIG. 1, at step 110, the TEE image is mapped to the 3D coordinate system of fluoroscopic image acquisition device (e.g., C-arm device) based on the estimated pose of the probe in the 3D coordinate system. In particular, the TEE is mapped to the 3D coordinate system based on the estimated pose of the probe using Ultrasound calibration parameters. The ultrasound device (i.e., the TEE transducer is calibrated offline prior to the cardiac procedure, resulting in ultrasound calibration parameters. The ultrasound calibration parameters are used to estimate a transform that relates the coordinate system of the TEE image to the local coordinate system of the head of the TEE ultrasound probe. Since the pose of the probe is estimated in the 3D coordinate system of the fluoroscopic image acquisition device, the transform maps the TEE image to the 3D coordinate system of the fluoroscopic image acquisition device based on the relationship between the head of the TEE ultrasound probe and the TEE image. The calculation of the transform from the ultrasound calibration parameters may be performed using the method described in Gao et al., "Rapid Image Registration of Three-Dimensional Transesophageal Echocardiography and X-ray Fluoroscopy for the Guidance of Cardiac Interventions", In *Proceedings of the First International Conference on Information Processing in Computer-Assisted Interventions*, 2010, pages 124-134, which is incorporated herein by reference. FIG. 7 illustrates a TEE image 702 mapped to the 3D local coordinate system of a fluoroscopic image acquisition device based on the pose of the ultrasound probe 704.

Figure 8:
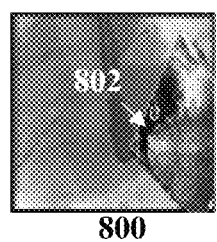
FIG. 8 illustrates a TEE image projected into a fluoroscopic image.

At step 112, the TEE image is projected into the fluoroscopic image to visualize the registration results. In particular, since TEE image is transformed to the coordinate system of the fluoroscopic image acquisition device (e.g., C-arm device) in step 110, the ultrasound plane of the TEE image can be projected into the fluoroscopic image using projection matrix associated with the fluoroscopic image. The resulting image can be displayed, for example, on a display of a computer system. FIG. 8 illustrates a TEE image 802 projected into a fluoroscopic image 800.

Returning to FIG. 1, at step 114, a 3D patient specific physiological model is detected in the TEE image. In a possible implementation, a holistic four-dimensional model of the left heart that includes its core anatomical structures of: left ventricle (LV), left atrium (LA), aortic valve (AV), mitral valve (MV), and papillary muscles (APM and PPM) can be detected in the TEE image. Given the physiological complexity of the left heart, a modular and hierarchical approach can be used for detecting the patient specific model, which facilitates capturing a broad spectrum of morphological and pathological variations. The patient-specific parameters of the physiological models can be estimated from 2D, 2×2D, or 3D ultrasound images using robust learning-based algorithms using hierarchical approaches within the Marginal Space Learning (MSL) and Trajectory spectrum learning (TSL) frameworks. Detectors can be trained using the Probabilistic Boosting Tree (PBT) with Haar and steerable features, and consequently applied to estimate the global location and motion followed by anatomical landmarks and surface structures. Methods for detecting physiological models using MSL and TSL are described United States Publication No. 2012/0022843, United States Publication No. 2011/0060576, Ionasec et al., "Patient-Specific Modeling and Quantification of the Aortic and Mitral Valves from 4D Cardiac CT and TEE", *IEEE*

Figure 9:
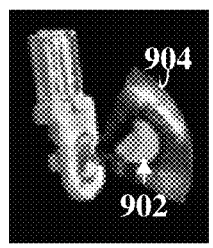
FIG. 9 illustrates a patient specific anatomical model estimated in a TEE image.

*Transactions on Medical Imaging*, 2010, and Ionasec et al., "Robust Motion Estimation Using Trajectory Spectrum Learning: Application to Aortic and Mitral Valve Modeling from 4D TEE", *Proceedings of 12th IEEE International Conference on Computer Vision*, 2008, pages 1601-1608, the disclosures of which are incorporated herein by reference. FIG. 9 illustrates a patient specific anatomical model 902 estimated in a TEE image 904.

At step 116, the patient specific model is projected into the fluoroscopic image. The model is estimated in the ultrasound (TEE) image space, and can therefore be transformed into the fluoroscopic image space using ultrasound calibration parameters and the projection matrix associated with the fluoroscopic image, as described above in steps 110 and 112.

Figure 10:
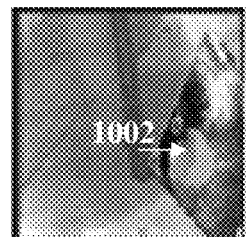
FIG. 10 illustrates a patient-specific model projected into a fluoroscopic image.

As described above, the registration results can be visualized by projecting the TEE image into the fluoroscopic image (step 112) or by projecting a patient specific model into the fluoroscopic image (step 114). It is also possible that the registration results can be visualized by displaying the fluoroscopic image and the TEE image as side-aligned images aligned to the same coordinate system. FIG. 10 illustrates a patient-specific model 1002 projected into a fluoroscopic image 1000.

The method of FIG. 1 may be repeated for each frame in a sequence of fluoroscopic images. In this case, the method of FIG. 1 can provide real time registration of TEE images to frames of the fluoroscopic image sequence during a cardiac procedure.

Figure 11:
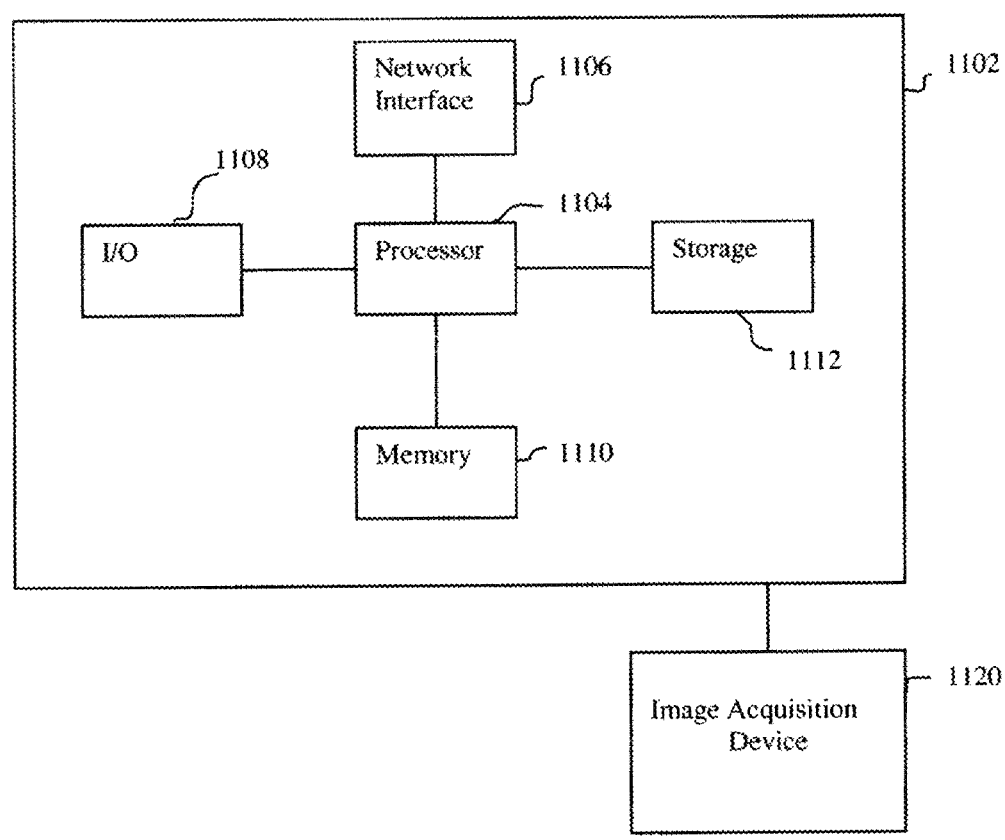
FIG. 11 is a high-level block diagram of a computer capable of implementing the present invention.

The above-described methods for registering ultrasound and patient specific physiological models to x-ray fluoroscopy images may be implemented on a computer using well-known computer processors, memory units, storage devices, computer software, and other components. A high-level block diagram of such a computer is illustrated in FIG. 11. Computer 1102 contains a processor 1104, which controls the overall operation of the computer 1102 by executing computer program instructions which define such operation. The computer program instructions may be stored in a storage device 1112 (e.g., magnetic disk) and loaded into memory 1110 when execution of the computer program instructions is desired. Thus, the steps of the methods of FIGS. 1, 4, and 5 may be defined by the computer program instructions stored in the memory 1110 and/or storage 1112 and controlled by the processor 1104 executing the computer program instructions. An image acquisition device 1120, such as a C-arm image acquisition device, can be connected to the computer 1102 to input image data to the computer 1102. It is possible to implement the image acquisition device 1120 and the computer 1102 as one device. It is also possible that the image acquisition device 1120 and the computer 1102 communicate wirelessly through a network. The computer 1102 also includes one or more network interfaces 1106 for communicating with other devices via a network. The computer 1102 also includes other input/output devices 1108 that enable user interaction with the computer 1102 (e.g., display, keyboard, mouse, speakers, buttons, etc.). One skilled in the art will recognize that an implementation of an actual computer could contain other components as well, and that FIG. 11 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for registering an ultrasound image acquired using an ultrasound probe to a fluoroscopic image acquired using a fluoroscopic image acquisition device, comprising:
    detecting a 2D location of the ultrasound probe in the fluoroscopic image using a trained machine learning based probe detector that extracts features from image patches of the fluoroscopic image, determines a probability score for each image patch, and selects the image patch having the highest probability score as the 2D location of the ultrasound probe;
    estimating an initial machine learning based 3D pose of the ultrasound probe based on the detected 2D location of the ultrasound probe in the fluoroscopic image by initializing pose estimation using X and Y coordinates estimated from the detected 2D location of the ultrasound probe, estimating a 3D position of the ultrasound probe including X, Y, and Z coordinates based on the X and Y coordinates estimated from the detected 2D location by applying a trained machine learning based position classifier to the fluoroscopic image, and estimating a 3D position and orientation of the ultrasound probe including X, Y, and Z coordinates and a roll, pitch, and yaw based on the 3D position estimating using the trained machine learning based position classifier by applying a trained machine learning based position and orientation classifier to the fluoroscopic image;
    iteratively refining the estimated initial machine learning based 3D pose of the ultrasound probe using 2D/3D registration based on the ultrasound and the fluoroscopic image to estimate a final 3D pose of the ultrasound probe;
    mapping the ultrasound image to a 3D coordinate system of the fluoroscopic image acquisition device based on the estimated final 3D pose of the ultrasound probe;
    estimating a patient specific physiological model of an anatomical structure in the ultrasound image; and
    projecting the patient specific physiological model of the anatomical structure into the fluoroscopic image using a projection matrix associated with the fluoroscopic image.

2. The method of claim 1, wherein the fluoroscopic image is a frame in a fluoroscopic image sequence the step of detecting a 2D location of the ultrasound probe in the fluoroscopic image comprises:
    determining a reduced search space in the fluoroscopic image based on a probe location predicted from a detected probe location in a previous frame in the fluoroscopic image sequence; and
    detecting the 2D location of the ultrasound probe in the reduced search space using a trained probe detector.

3. The method of claim 1, wherein the estimated final 3D pose is a position and orientation of the ultrasound probe in the 3D coordinate system of the fluoroscopic image acquisition device used to acquire the fluoroscopic image.

4. The method of claim 3, wherein the step of mapping the ultrasound image to a 3D coordinate system of the fluoroscopic image acquisition device based on the estimated final 3D pose of the ultrasound probe comprises:

calculating a transform to map the ultrasound image to the 3D coordinate system of the fluoroscopic image acquisition device based on the position and orientation of the ultrasound probe corresponding to the estimated final 3D pose using ultrasound configuration parameters.

5. The method of claim 1, wherein the step of iteratively refining the estimated initial machine learning based 3D pose of the ultrasound probe using 2D/3D registration based on the ultrasound and the fluoroscopic image to estimate a final 3D pose of the ultrasound probe comprises:
   (a) aligning a 3D model of the ultrasound probe to current estimated 3D pose;
   (b) generating a digital reconstructed radiograph (DRR) from the aligned 3D model of the ultrasound probe;
   (c) measuring a difference value between the fluoroscopic image and the DRR; and
   (d) refining the current estimated 3D pose to reduce the difference value between the fluoroscopic image and the DRR.

6. The method of claim 5, wherein the step of iteratively refining the estimated initial machine learning based 3D pose of the ultrasound probe using 2D/3D registration based on the ultrasound and the fluoroscopic image to estimate a final 3D pose of the ultrasound probe further comprises:
   (e) repeating steps (a)-(d) until the difference value between the fluoroscopic image and the DRR is less than a threshold.

7. The method of claim 1, further comprising:
   projecting the ultrasound image into the fluoroscopic image using a projection matrix associated with the fluoroscopic image.

8. The method of claim 1, wherein the ultrasound image is a transesophageal echocardiography (TEE) image and the ultrasound probe is a TEE ultrasound probe used to acquire the TEE image.

9. An apparatus for registering an ultrasound image acquired using an ultrasound probe to a fluoroscopic image acquired using a fluoroscopic image acquisition device, comprising:
   a processor; and
   a memory storing computer program instructions, which when executed by the processor cause the processor to perform operations comprising:
   detecting a 2D location of the ultrasound probe in the fluoroscopic image using a trained machine learning based probe detector that extracts features from image patches of the fluoroscopic image, determines a probability score for each image patch, and selects the image patch having the highest probability score as the 2D location of the ultrasound probe;
   estimating an initial machine learning based 3D pose of the ultrasound probe based on the detected 2D location of the ultrasound probe in the fluoroscopic image by initializing pose estimation using X and Y coordinates estimated from the detected 2D location of the ultrasound probe, estimating a 3D position of the ultrasound probe including X, Y, and Z coordinates based on the X and Y coordinates estimated from the detected 2D location by applying a trained machine learning based position classifier to the fluoroscopic image, and estimating a 3D position and orientation of the ultrasound probe including X, Y, and Z coordinates and a roll, pitch, and yaw based on the 3D position estimating using the trained machine learning based position classifier by applying a trained machine learning based position and orientation classifier to the fluoroscopic image;
   iteratively refining the estimated initial machine learning based 3D pose of the ultrasound probe using 2D/3D registration based on the ultrasound and the fluoroscopic image to estimate a final 3D pose of the ultrasound probe;
   mapping the ultrasound image to a 3D coordinate system of the fluoroscopic image acquisition device based on the estimated final 3D pose of the ultrasound probe;
   estimating a patient specific physiological model of an anatomical structure in the ultrasound image; and
   projecting the patient specific physiological model of the anatomical structure into the fluoroscopic image.

10. The apparatus of claim 9, wherein the estimated final 3D pose of the ultrasound probe is a position and orientation of the ultrasound probe in the 3D coordinate system of the fluoroscopic image acquisition device.

11. The apparatus of claim 10, wherein mapping the ultrasound image to a 3D coordinate system of the fluoroscopic image acquisition device based on the estimated final 3D pose of the ultrasound probe comprises:
   calculating a transform to map the ultrasound image to the 3D coordinate system of the fluoroscopic image acquisition device based on the position and orientation of the ultrasound probe corresponding to the estimated final 3D pose using ultrasound configuration parameters.

12. The apparatus of claim 9, further comprising:
   means for projecting the ultrasound image into the fluoroscopic image.

13. A non-transitory computer readable medium encoded with computer executable instructions which when executed by a processor cause the processor to perform a method for registering an ultrasound image acquired using an ultrasound probe to a fluoroscopic image acquired using a fluoroscopic image acquisition device, the method comprising:
   detecting a 2D location of the ultrasound probe in the fluoroscopic image using a trained machine learning based probe detector that extracts features from image patches of the fluoroscopic image, determines a probability score for each image patch, and selects the image patch having the highest probability score as the 2D location of the ultrasound probe;
   estimating an initial machine learning based 3D pose of the ultrasound probe based on the detected 2D location of the ultrasound probe in the fluoroscopic image by initializing pose estimation using X and Y coordinates estimated from the detected 2D location of the ultrasound probe, estimating a 3D position of the ultrasound probe including X, Y, and Z coordinates based on the X and Y coordinates estimated from the detected 2D location by applying a trained machine learning based position classifier to the fluoroscopic image, and estimating a 3D position and orientation of the ultrasound probe including X, Y, and Z coordinates and a roll, pitch, and yaw based on the 3D position estimating using the trained machine learning based position classifier by applying a trained machine learning based position and orientation classifier to the fluoroscopic image;
   iteratively refining the estimated initial machine learning based 3D pose of the ultrasound probe using 2D/3D registration based on the ultrasound and the fluoroscopic image to estimate a final 3D pose of the ultrasound probe;

mapping the ultrasound image to a 3D coordinate system of the fluoroscopic image acquisition device based on the estimated final 3D pose of the ultrasound probe;

estimating a patient specific physiological model of an anatomical structure in the ultrasound image; and projecting the patient specific physiological model of the anatomical structure into the fluoroscopic image using a projection matrix associated with the fluoroscopic image.

14. The non-transitory computer readable medium of claim 13, wherein the fluoroscopic image is a frame in a fluoroscopic image sequence the step of detecting a 2D location of the ultrasound probe in the fluoroscopic image comprises:

determining a reduced search space in the fluoroscopic image based on a probe location predicted from a detected probe location in a previous frame in the fluoroscopic image sequence; and detecting the 2D location of the ultrasound probe in the reduced search space using a trained probe detector.

15. The non-transitory computer readable medium of claim 13, wherein the estimated final 3D pose of the ultrasound probe is a position and orientation of the ultrasound probe in the 3D coordinate system of the fluoroscopic image acquisition device.

16. The non-transitory computer readable medium of claim 15, wherein the step of mapping the ultrasound image to a 3D coordinate system of the fluoroscopic image acquisition device based on the estimated final 3D pose of the ultrasound probe comprises:

calculating a transform to map the ultrasound image to the 3D coordinate system of the fluoroscopic image acquisition device based on the position and orientation of the ultrasound probe corresponding to the estimated final 3D pose using ultrasound configuration parameters.

17. The non-transitory computer readable medium of claim 16, wherein the step of iteratively refining the estimated initial machine learning based 3D pose of the ultrasound probe using 2D/3D registration based on the ultrasound and the fluoroscopic image to estimate a final 3D pose of the ultrasound probe comprises:

(a) aligning a 3D model of the ultrasound probe to current estimated 3D pose;

(b) generating a digital reconstructed radiograph (DRR) from the aligned 3D model of the ultrasound probe;

(c) measuring a difference value between the fluoroscopic image and the DRR; and (d) refining the current estimated 3D pose to reduce the difference value between the fluoroscopic image and the DRR.

18. The non-transitory computer readable medium of claim 17, wherein the step of iteratively refining the estimated initial machine learning based 3D pose of the ultrasound probe using 2D/3D registration based on the ultrasound and the fluoroscopic image to estimate a final 3D pose of the ultrasound probe further comprises:

(e) repeating steps (a)-(d) until the difference value between the fluoroscopic image and the DRR is less than a threshold.

19. The non-transitory computer readable medium of claim 13, the method further comprising:

projecting the ultrasound image into the fluoroscopic image using a projection matrix associated with the fluoroscopic image.

20. The method of claim 1, wherein estimating a patient specific physiological model of an anatomical structure in the ultrasound image comprises:

estimating the patient specific physiological model of the anatomical structure in the ultrasound image using one of marginal space learning (MSL) or trajectory spectrum learning (TSL).

* * * * *